(12) United States Patent
Oh

(10) Patent No.: US 11,255,081 B2
(45) Date of Patent: Feb. 22, 2022

(54) URINAL SCREEN

(71) Applicant: Jay K Oh, Wycoff, NJ (US)

(72) Inventor: Jay K Oh, Wycoff, NJ (US)

( * ) Notice: Subject to any disclaimer, the term of this patent is extended or adjusted under 35 U.S.C. 154(b) by 408 days.

(21) Appl. No.: 16/587,481

(22) Filed: Sep. 30, 2019

(65) Prior Publication Data

US 2021/0095458 A1 Apr. 1, 2021

(51) Int. Cl.
*E03D 13/00* (2006.01)
*G01N 33/52* (2006.01)
*G01N 1/20* (2006.01)

(52) U.S. Cl.
CPC ............. *E03D 13/005* (2013.01); *G01N 1/20* (2013.01); *G01N 33/521* (2013.01)

(58) Field of Classification Search
CPC ...... E03D 13/005; G01N 1/20; G01N 33/521; A61B 10/007; A61B 2010/0006; C12Q 1/54
See application file for complete search history.

(56) References Cited

U.S. PATENT DOCUMENTS

| | | | |
|---|---|---|---|
| 3,817,239 A | 6/1974 | Kuntz | |
| 4,554,687 A | 11/1985 | Carter | |
| 4,636,474 A | 1/1987 | Ogura | |
| 4,901,736 A | 2/1990 | Huang | |
| 5,604,937 A * | 2/1997 | Davenport | E03D 13/00 4/222.1 |
| 5,730,149 A | 3/1998 | Nakayama | |
| 9,616,165 B2 | 4/2017 | Larson | |
| 2012/0165626 A1* | 6/2012 | Irina | A61B 10/0064 600/316 |
| 2018/0003621 A1* | 1/2018 | Drury | G01N 33/493 |
| 2018/0055488 A1 | 3/2018 | Hall | |

* cited by examiner

*Primary Examiner* — Jennifer Wecker
*Assistant Examiner* — Kathryn Elizabeth Limbaugh
(74) *Attorney, Agent, or Firm* — JIKIM LLC—Attorneys at Law; Jisang Kim, Esq

(57) ABSTRACT

The present invention is a urinal screen that includes a main body having an extended upper surface, a corresponding extended lower surface, and a marginal edge portion integral with an surrounding the upper surface and the lower surface; a plurality of spaced apart apertures formed to extent through the main body to provide fluid communication between the upper surface and the lower surface of the main body; and a two-sided spreading layer attached to the main body for accepting a urine sample on a upper side and passing the sample to a lower side, opposite and each side containing a reagent that can react with glucose in the urine sample, as it passes through the two-sided spreading layer, to cause a color change in the reagent.

20 Claims, 4 Drawing Sheets

URINAL SCREEN

TECHNICAL FIELD & BACKGROUND

The present invention generally related to a urinal screen, and in particular, to an improved urinal screen.

The typical use of a urinal screen is either to prevent large debris from entering a urinal drain causing a blockage or to capture odors found in a men's restroom.

People with diabetes often uses a urine dipstick test to measure glucose levels which requires spotting subtle color differences on the stick.

The steps involved in such urine dipstick test are as follows: (1) wash hands with soap and dry well, (2) collect a fresh urine sample in a clean, dry cup, (3) take one urine glucose test strip, (4) dip the test areas of the strip in the urine, and (5) observe the change in color of the test strip.

As described above, the conventional steps involved in measuring glucose levels require at least 4 or 5 steps. This kind of traditional method obviously inconveniences people.

Therefore, it would be desirable to provide an improved urinal screen that could be used to measure glucose levels and could eliminate such inconvenience steps involved in measuring glucose levels.

SUMMARY OF THE INVENTION

The present invention is directed to a urinal screen that overcomes the above-mentioned disadvantages of the prior art.

In one aspect, the present invention provides a urinal screen having a main body, a plurality of spaced apart apertures formed to extent through the main body, a mesh screen, and a two-sided spreading layer. The main body has an extended upper surface, a corresponding extended lower surface, and a marginal edge portion integral with and surrounding the upper surface and the lower surface. The main body is sized and shaped to be placed in a urinal and is configured to extend over a portion of the drain portion of the urinal. The plurality of spaced apart apertures is formed to extent through the main body to provide fluid communication between the upper surface and the lower surface of the main body. The mesh screen has a upper surface, a lower surface, and a plurality of spaced apart apertures formed to extent through the mesh screen to provide fluid communication between the upper surface and the lower surface of said mesh screen. The mesh screen has a perimeter and includes a thin solid band encasing said perimeter. The mesh screen is attached to the main body. The two-sided spreading layer is to accept a urine sample on a upper side and passing the sample to a lower side, opposite and each side containing a reagent that can react with glucose in the urine sample, as it passes through the two-sided spreading layer, to cause a color change in the reagent. The two-sided spreading layer is attached to the main body.

In another aspect, the present invention provides a urinal screen having a main body, a plurality of spaced apart apertures formed to extent through the main body, and a two-sided spreading layer. The main body has an extended upper surface, a corresponding extended lower surface, and a marginal edge portion integral with and surrounding the upper surface and the lower surface. The main body is sized and shaped to be placed in a urinal and is configured to extend over a portion of the drain portion of the urinal. The plurality of spaced apart apertures is formed to extent through the main body to provide fluid communication between the upper surface and the lower surface of the main body. The two-sided spreading layer is to accept a urine sample on a upper side and passing the sample to a lower side, opposite and each side containing a reagent that can react with glucose in the urine sample, as it passes through the two-sided spreading layer, to cause a color change in the reagent. The two-sided spreading layer is attached to the main body.

In a further aspect, the present invention provides a urinal screen having a main body, a plurality of spaced apart apertures formed to extent through the main body, a flexible member, and a two-sided spreading layer. The main body has an extended upper surface, a corresponding extended lower surface, a perimeter, and a marginal edge portion integral with and surrounding the upper surface and the lower surface. The main body is sized and shaped to be placed in a urinal and is configured to extend over a portion of the drain portion of the urinal. The plurality of spaced apart apertures is formed to extent through the main body to provide fluid communication between the upper surface and the lower surface of the main body. The flexible member encases the perimeter of the main body. The two-sided spreading layer is to accept a urine sample on a upper side and passing the sample to a lower side, opposite and each side containing a reagent that can react with glucose in the urine sample, as it passes through the two-sided spreading layer, to cause a color change in the reagent. The two-sided spreading layer is attached to the main body.

BRIEF DESCRIPTION OF THE DRAWINGS

The present invention will be described by way of exemplary embodiments, but not limitations, illustrated in the accompanying drawing in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

This present invention provides a urinal screen that permits fast determination of glucose levels using a sample of urine without the need for a urine dipstick or a meter.

Figure 1:
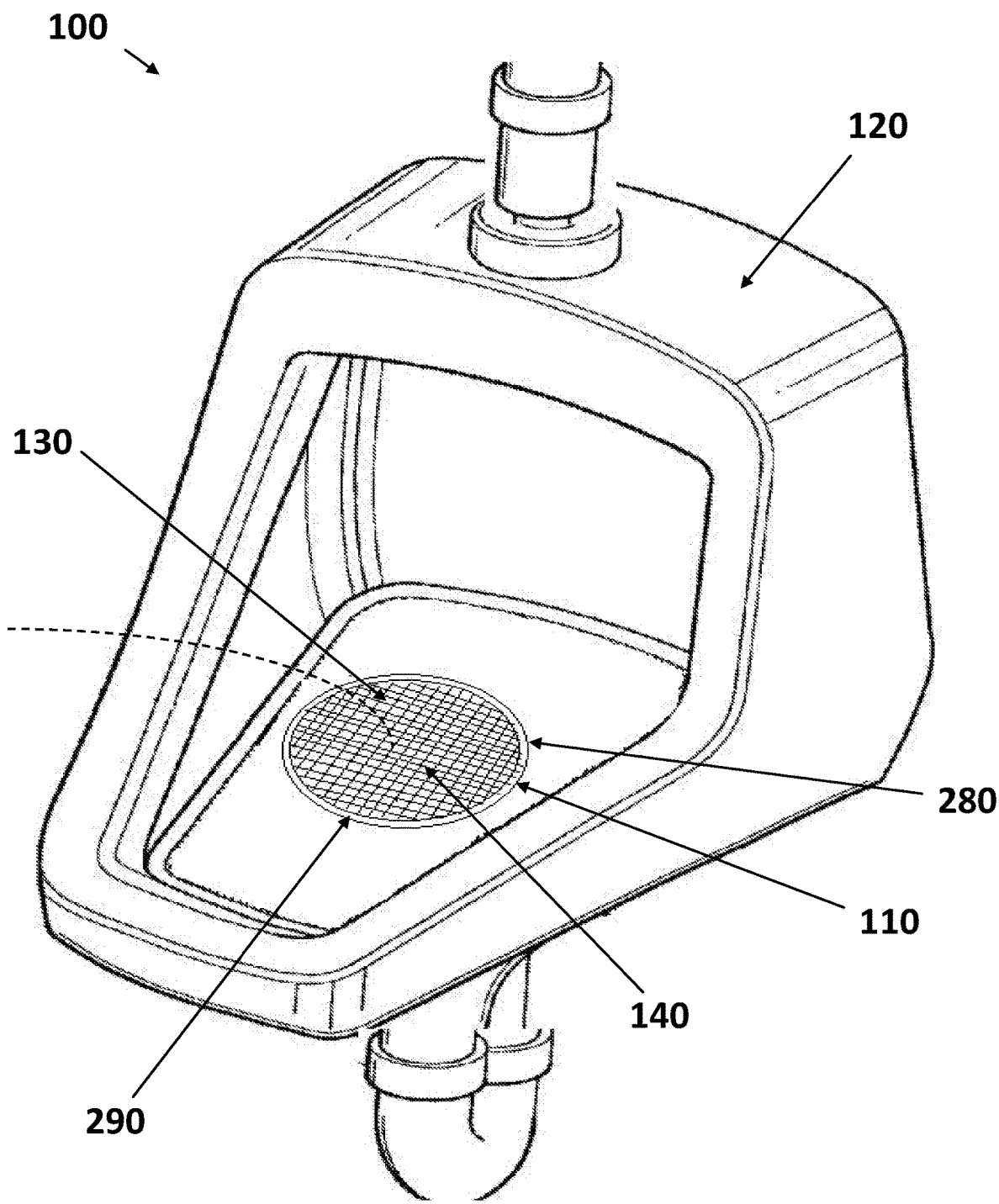
FIG. 1 illustrates a perspective view of a urinal screen, in accordance with one embodiment of the present invention.
Figure 2:
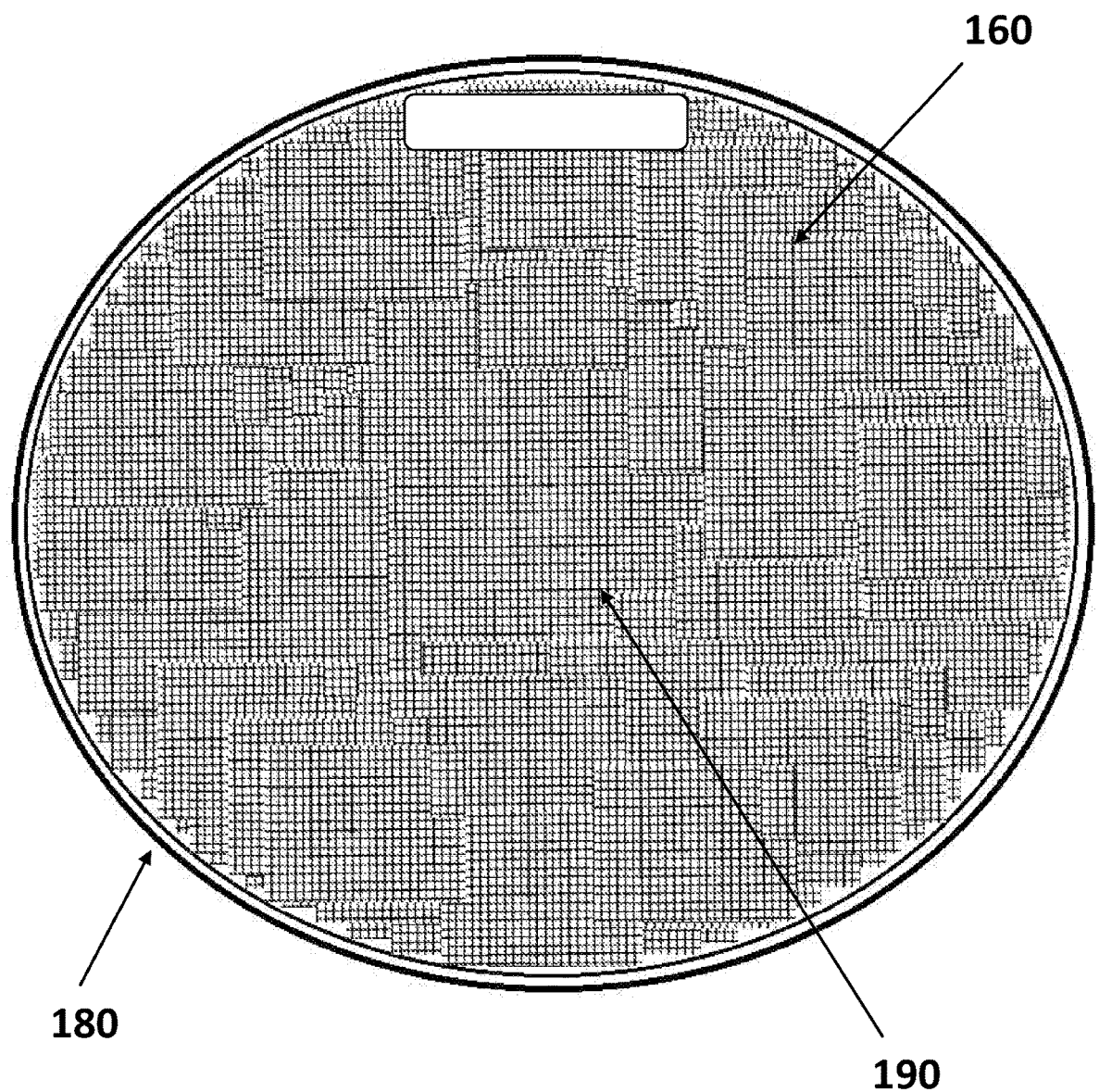
FIG. 2 illustrates a top plan view of a urinal screen, in accordance with one embodiment of the present invention.
Figure 3:
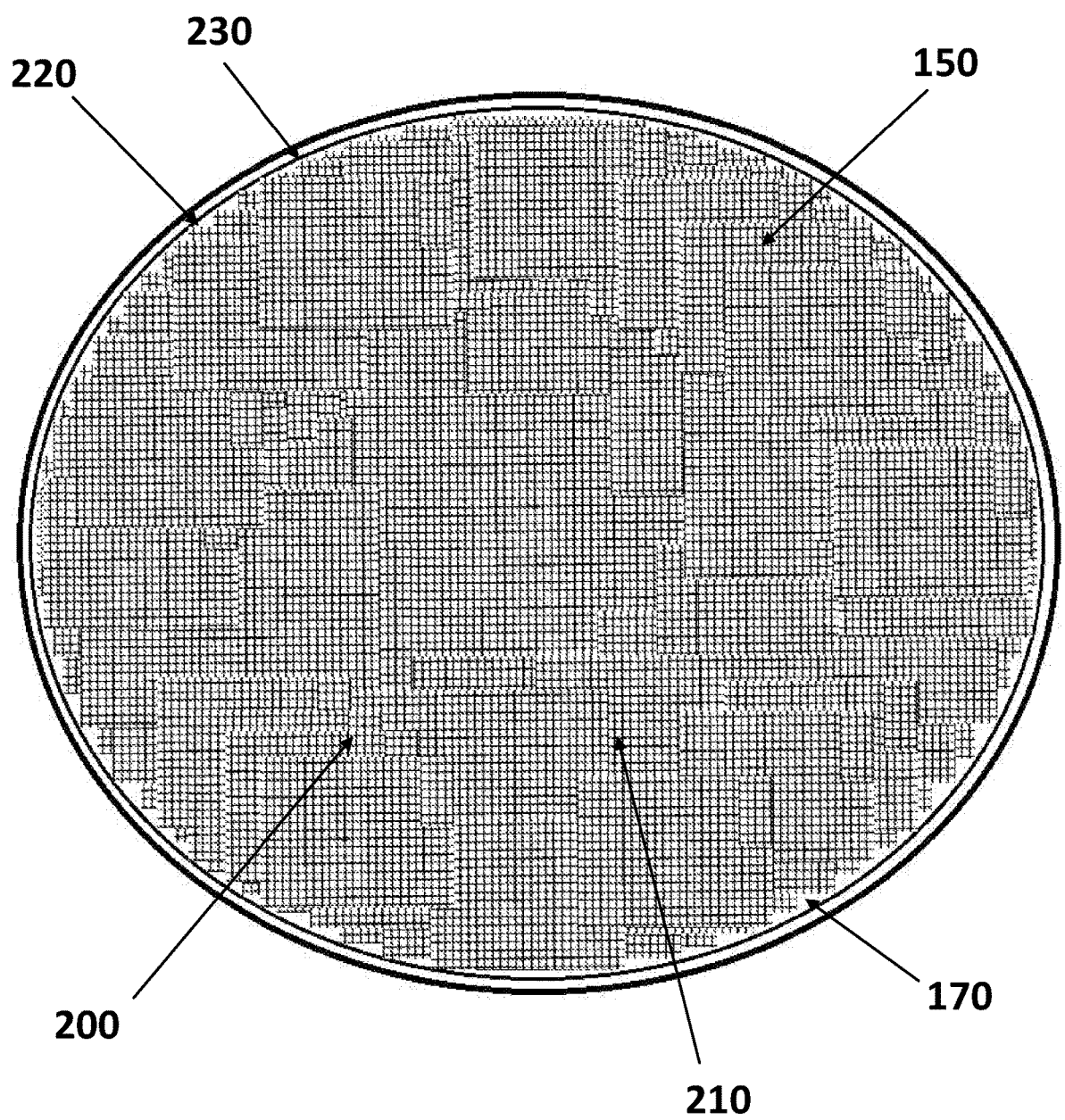
FIG. 3 illustrates a bottom plan view of a urinal screen, in accordance with one embodiment of the present invention.
Figure 4:
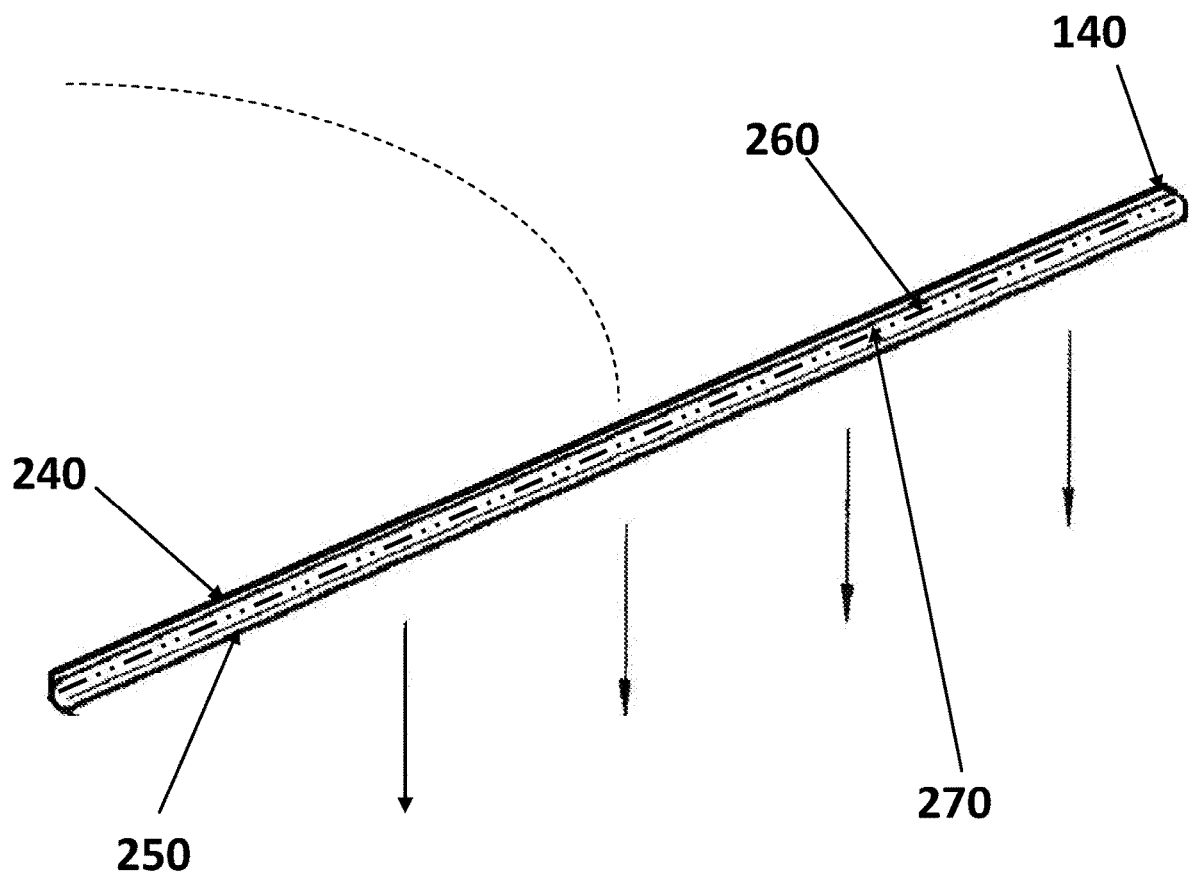
FIG. 4 illustrates a side view of a urinal screen, in accordance with one embodiment of the present invention.

FIG. 1 illustrates a perspective view of a urinal screen, in accordance with one embodiment of the present invention. FIG. 2 illustrates a top plan view of a urinal screen, in accordance with one embodiment of the present invention. FIG. 3 illustrates a bottom plan view of a urinal screen, in accordance with one embodiment of the present invention. FIG. 4 illustrates a side view of a urinal screen, in accordance with one embodiment of the present invention.

Referring to FIGS. 1, 2, 3, and 4, the urinal screen 100 includes a main body 110, a plurality of spaced apart apertures 130 formed to extent through the main body 110, a mesh screen 150, a flexible member 280, and a two-sided spreading layer 140.

The main body 110 has an extended upper surface 160, a corresponding extended lower surface 170, a perimeter 290, and a marginal edge portion 180 integral with and surrounding the upper surface 160 and the lower surface 170. The main body 110 is sized and shaped to be placed in a urinal 120 and is configured to extend over a portion of the drain portion of the urinal 120. The plurality of spaced apart apertures 130 is formed to extent through the main body 110 to provide fluid communication between the upper surface 160 and the lower surface 170 of the main body 110. The flexible member 280 encases the perimeter 290 of the main body 110.

The mesh screen has a upper surface 190, a lower surface 200, and a plurality of spaced apart apertures 210 formed to extent through the mesh screen 150 to provide fluid communication between the upper surface 190 and the lower surface 200 of said mesh screen. The mesh screen 150 has a perimeter 220 and includes a thin solid band 230 encasing said perimeter 220. The mesh screen 150 is attached to the main body 110. The two-sided spreading layer 140 is to accept a urine sample on a upper side 240 and passing the sample to a lower side 250, opposite and each side containing a reagent 260 that can react with glucose in the urine sample, as it passes through the two-sided spreading layer 140, to cause a color change in the reagent 260. The two-sided spreading layer 140 is attached to the main body 110.

Additionally, the man body 110 can also include a flexible member 280. The flexible member 280 encases the perimeter 290 of the main body 110.

The main body 110, mesh screen 150, the flexible member 280, and the two-sided spreading layer 140 can be made of a plastic or rubber which can resist damage or alteration due to the environmental conditions within a urinal 120. The apertures 130 are larger in the upper surface 160 and decrease in size toward the lower surface 170. The main body 110 and the mesh screen 150 can also be fabricated from a metallic material. Further, the mesh screen 150 has a perimeter 220 and includes a thin solid band 230 encasing the perimeter. A logo can also be inscribed on the upper surface 160 of the main body 110. In operation, the urinal screen 100 is place over a drain as illustrated clearly in FIG. 1. In order to use the urinal screen 100 for measuring glucose levels, it is required to first place the main body 110 in the urinal 120 to extend over the portion of the drain portion of the urinal 120. In this process, the upper surface 160 of the main body 110 is supported to maintain horizontality without inclining to aside within the drain portion of the urinal 120. In operation a urine sample is applied to spreading the upper side 240 of the layer 140. As the urine sample penetrates the layer 140, it spreads out, so that sample is substantially uniformly distributed to the layer 140. The layer contains a reagent 260 and membrane 270. Membrane 270 also contains a reagent 260 that reacts with glucose to cause a visible change in color. Membrane 270 contains a reagent 260 that also reacts with glucose to cause a color change, but the color formed in different from that formed in the layer. Glucose in the urine sample reacts with the reagents in membranes 270 and the layer 140 as it passes toward the layer 140 to form colors. A variety of materials are suitable for the spreading layer 140; for example, paper, glass fibers, polymer fibers, plastics, woven and non-woven fabrics, and membranes. Preferred materials require minimum sample sizes, absorb the sample quickly, and distribute it uniformly to the membranes and the layer. Further, preferred materials of the main body 110, the mesh screen 150, the flexible member 280, the thin solid band 230, and the layer 140 is typically formed of non-toxic plastic or rubber so as to keep the cost of such screen at a minimum, to facilitate sterilization, and also to provide the necessary inherent flexibility and resiliency needed for the urinal screen 100 to fit onto the portion of the drain portion of the urinal 120.

Thus, the urinal screen 100 disclosed herein enables people to considerably reduce the period and the cost for measuring glucose levels because the present invention permits fast determination of glucose levels by using the layer 140 attached to the main body 110 of the urinal screen 100 without the need for a urine dipstick or a meter.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A urinal screen, comprising:
   a main body having an extended upper surface, a corresponding extended lower surface, and a marginal edge portion integral with and surrounding the upper surface and the lower surface; wherein the main body is configured to fit onto a portion of the drain portion of the urinal;
   a plurality of spaced apart apertures formed to extent through the main body to provide fluid communication between the upper surface and the lower surface of the main body;
   a mesh screen having a upper surface, a lower surface, and a plurality of spaced apart apertures formed to extent through the mesh screen to provide fluid communication between the upper surface and the lower surface of said mesh screen; wherein the mesh screen has a perimeter and includes a thin solid band encasing said perimeter, wherein the mesh screen is attached to the main body; and
   a two-sided spreading layer for accepting a urine sample on a upper side and passing the sample to a lower side, opposite from the upper side, and each side of the two-sided spreading layer containing a reagent, wherein the reagent disposed on both sides of the spreading layer is configured to react with glucose in the urine sample, as it passes through the two-skied spreading layer configured to cause a color change in the reagent on both sides of the spreading layer, wherein the two-sided spreading layer is attached to the main body.

2. The urine screen according to claim 1, wherein the main body, mesh screen and the two-sided spreading layer are made of a plastic, wherein the plastic resists damage or alteration due to the environmental conditions within a urinal.

3. The urine screen according to claim 1, wherein the apertures are larger in the upper surface and decrease in size toward the lower surface.

4. The urine screen according to claim 1, wherein the main body is fabricated from a metallic material.

5. The urine screen according to claim 1, wherein the mesh screen is fabricated from a metallic material.

6. The urine screen according to claim 1, wherein the main body has a perimeter and includes a flexible member encasing the perimeter.

7. The urine screen according to claim 1, wherein a logo is inscribed on the upper surface of the main body.

8. A urinal screen, comprising:
 a main body having an extended upper surface, a corresponding extended lower surface, and a marginal edge portion integral with and surrounding the upper surface and the lower surface; wherein the main body is configured to fit onto a portion of the drain portion of the urinal;
 a plurality of spaced apart apertures formed to extent through the main body to provide fluid communication between the upper surface and the lower surface of the main body; and
 a two-sided spreading layer for accepting a urine sample on a upper side and passing the sample to a lower side, opposite from the upper side, and each side of the two-sided spreading layer containing a reagent, wherein the reagent disposed on both sides of the spreading layer is configured to react with glucose in the urine sample, as it passes through the two-sided spreading layer and, which is configured to cause a color change in the reagent on both sides of the spreading layer, wherein the two-sided spreading layer is attached to the main body.

9. The urine screen according to claim 8, wherein the main body and the two-sided spreading layer are made of a plastic, wherein the plastic resists damage or alteration due to the environmental conditions within a urinal.

10. The urine screen according to claim 8, wherein the apertures are larger in the upper surface and decrease in size toward the lower surface.

11. The urine screen according to claim 8, wherein the main body is fabricated from a metallic material.

12. The urine screen according to claim 8, wherein the two-sided spreading layer is fabricated from a metallic material.

13. The urine screen according to claim 8, wherein the main body has a perimeter and includes a flexible member encasing the perimeter.

14. The urine screen according to claim 8, wherein a logo is inscribed on the upper surface of the main body.

15. A urinal screen, comprising:
 a main body having an extended upper surface, a corresponding extended lower surface, and a marginal edge portion integral with and surrounding the upper surface and the lower surface; wherein the main body is configured to fit onto a portion of the drain portion of the urinal;
 a plurality of spaced apart apertures formed to extent through the main body to provide fluid communication between the upper surface and the lower surface of the main body;
 a flexible member encasing the perimeter of the main body; and
 a two-sided spreading layer for accepting a urine sample on a upper side and passing the sample to a lower side, opposite from the upper side, and each side of the two-sided spreading layer containing a reagent, wherein the reagent disposed on both sides of the spreading layer is configured to react with glucose in the urine sample, as it passes through the two-sided spreading layer and, configured to cause a color change in the reagent on both sides of the spreading layer, wherein the two-sided spreading layer is attached to the main body.

16. The urine screen according to claim 15, wherein the main body and the mesh screen are made of a plastic, wherein the plastic resists damage or alteration due to the environmental conditions within a urinal.

17. The urine screen according to claim 15, wherein the apertures are larger in the upper surface and decrease in size toward the lower surface.

18. The urine screen according to claim 15, wherein the main body is fabricated from a metallic material.

19. The urine screen according to claim 15, wherein the flexible member is made of a plastic or rubber.

20. The urine screen according to claim 15, wherein a logo is inscribed on the upper surface of the main body.

* * * * *